United States Patent
Jiang et al.

(10) Patent No.: US 12,029,828 B2
(45) Date of Patent: Jul. 9, 2024

(54) DISINFECTION CAP

(71) Applicant: Becton, Dickinson and Company, Franklin Lakes, NJ (US)

(72) Inventors: Chang Jiang, Butler, NJ (US); Narasinha C. Parasnis, Nanuet, NY (US); Amir Harandi, Bloomingdale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 283 days.

(21) Appl. No.: 17/183,917

(22) Filed: Feb. 24, 2021

(65) Prior Publication Data
US 2021/0275707 A1  Sep. 9, 2021

Related U.S. Application Data

(60) Provisional application No. 62/985,581, filed on Mar. 5, 2020.

(51) Int. Cl.
*A61L 2/26* (2006.01)
*A61L 2/18* (2006.01)

(52) U.S. Cl.
CPC ............ *A61L 2/26* (2013.01); *A61L 2/18* (2013.01); *A61L 2202/122* (2013.01); *A61L 2202/24* (2013.01)

(58) Field of Classification Search
CPC .......... A61L 2/18; A61L 2/26; A61L 2202/24; A61L 2202/122; A61M 39/16; A61M 39/20; A61M 39/162; A61M 2005/3104; A61M 2005/0205; A61M 2039/16; A61M 2039/0072
See application file for complete search history.

(56) References Cited

U.S. PATENT DOCUMENTS

| | | | |
|---|---|---|---|
| 3,403,679 | A | 10/1968 | Sinclair et al. |
| 4,417,890 | A | 11/1983 | Dennehey et al. |
| 4,597,758 | A | 7/1986 | Aalto et al. |
| 4,642,102 | A | 2/1987 | Ohmori |
| 4,711,363 | A | 12/1987 | Marino |
| 4,738,376 | A | 4/1988 | Markus |

(Continued)

FOREIGN PATENT DOCUMENTS

| | | |
|---|---|---|
| CA | 2803761 A1 | 12/2011 |
| CA | 2523133 C | 2/2013 |

(Continued)

OTHER PUBLICATIONS

"Non-Final Office Action in U.S. Appl. No. 17/076,102 dated Aug. 24, 2021, 10 pages".

(Continued)

*Primary Examiner* — Jennifer Wecker
*Assistant Examiner* — Brady C Pilsbury
(74) *Attorney, Agent, or Firm* — Servilla Whitney LLC

(57) ABSTRACT

A disinfection cap is described for connection to a medical connector, the disinfection cap including a housing having a top wall and sidewall forming a cavity, a blockage feature disposed on the top wall of the cavity, the blockage feature for fluidly blocking a hub of a luer connector, disinfectant or antimicrobial agent disposed within an open cell foam structure within the cavity. The open cell foam structure releasing the disinfectant or antimicrobial agent as the open cell foam structure is depressed by the hub of the luer connector.

13 Claims, 8 Drawing Sheets

(56) References Cited

U.S. PATENT DOCUMENTS

| | | | |
|---|---|---|---|
| 4,795,432 A | 1/1989 | Karczmer |
| 4,813,940 A | 3/1989 | Parry |
| 4,906,231 A | 3/1990 | Young |
| 4,950,250 A | 8/1990 | Haber et al. |
| 5,084,017 A | 1/1992 | Maffetone |
| 5,395,347 A | 3/1995 | Blecher et al. |
| 5,496,288 A | 3/1996 | Sweeny |
| 5,591,138 A | 1/1997 | Vaillancourt |
| 5,676,406 A | 10/1997 | Simmons et al. |
| 5,688,241 A | 11/1997 | Asbaghi |
| 5,755,696 A | 5/1998 | Caizza |
| 5,984,123 A | 11/1999 | Mogami et al. |
| 5,984,899 A | 11/1999 | D'Alessio et al. |
| RE36,885 E | 9/2000 | Blecher et al. |
| 6,565,529 B1 | 5/2003 | Kimber et al. |
| 6,632,199 B1 | 10/2003 | Tucker et al. |
| 6,884,237 B2 | 4/2005 | Asbaghi |
| 6,926,697 B2 | 8/2005 | Malenchek |
| 7,083,605 B2 | 8/2006 | Miyahara |
| 7,361,159 B2 | 4/2008 | Fiser et al. |
| 7,513,888 B2 | 4/2009 | Sircom et al. |
| 7,811,261 B2 | 10/2010 | Rubinstein et al. |
| 8,012,131 B2 | 9/2011 | Moser et al. |
| 8,062,265 B2 | 11/2011 | Millerd |
| 8,162,882 B2 | 4/2012 | Rubinstein et al. |
| 8,303,541 B2 | 11/2012 | Chun |
| 8,333,738 B2 | 12/2012 | Millerd |
| 8,388,894 B2 | 3/2013 | Colantonio |
| 8,439,870 B2 | 5/2013 | Moyer et al. |
| 8,496,627 B2 | 7/2013 | Chelak et al. |
| 8,636,688 B2 | 1/2014 | Shaw |
| 8,636,703 B2 | 1/2014 | Foshee et al. |
| 8,647,307 B2 | 2/2014 | Gratwohl et al. |
| 8,647,308 B2 | 2/2014 | Solomon et al. |
| 8,663,129 B2 | 3/2014 | Allen et al. |
| 8,715,231 B2 | 5/2014 | Woehr |
| 8,721,627 B2 | 5/2014 | Alpert et al. |
| 8,747,355 B2 | 6/2014 | Rubinstein et al. |
| 8,777,504 B2 | 7/2014 | Shaw et al. |
| 8,784,388 B2 | 7/2014 | Charles et al. |
| 8,827,961 B2 | 9/2014 | Emmott et al. |
| 8,961,475 B2 | 2/2015 | Solomon et al. |
| 8,968,241 B2 | 3/2015 | Liversidge |
| 8,979,794 B2 | 3/2015 | Chevallier |
| 9,039,989 B2 | 3/2015 | Lui et al. |
| 9,050,416 B2 | 6/2015 | Feret et al. |
| 9,061,106 B2 | 6/2015 | Roberts et al. |
| 9,067,024 B2 | 6/2015 | Roberts et al. |
| 9,132,223 B1 | 9/2015 | Wakeel |
| 9,186,466 B2 | 11/2015 | Zachek et al. |
| 9,192,449 B2 | 11/2015 | Kerr et al. |
| 9,352,099 B2 | 5/2016 | Roberts et al. |
| 9,352,100 B2 | 5/2016 | Ward et al. |
| 9,352,101 B2 | 5/2016 | Roberts et al. |
| 9,370,327 B2 | 6/2016 | Teoh |
| 9,399,125 B2 | 7/2016 | Burkholz |
| 9,408,632 B2 | 8/2016 | Erskine |
| 9,445,760 B2 | 9/2016 | Allen et al. |
| 9,694,140 B2 | 7/2017 | Rubinstein et al. |
| 9,848,810 B2 | 12/2017 | Allen et al. |
| 10,099,048 B2 | 10/2018 | Chiu et al. |
| 10,166,381 B2 | 1/2019 | Gardner et al. |
| 10,376,686 B2 | 8/2019 | Burkholz et al. |
| 10,589,080 B2 | 3/2020 | Hitchcock et al. |
| 10,603,481 B2 | 3/2020 | Avula et al. |
| 10,871,246 B2 | 12/2020 | Marici et al. |
| 11,353,147 B2 | 6/2022 | Marici |
| 11,511,100 B2 | 11/2022 | Ryan |
| 11,628,288 B1 | 4/2023 | Solomon et al. |
| 2003/0093009 A1 | 5/2003 | Newby et al. |
| 2003/0209681 A1 | 11/2003 | Leinsing et al. |
| 2004/0039341 A1 | 2/2004 | Ranalletta |
| 2005/0147525 A1 | 7/2005 | Bousquet |
| 2005/0197646 A1 | 9/2005 | Connell et al. |
| 2007/0060904 A1 | 3/2007 | Vedrine et al. |
| 2008/0010766 A1 | 1/2008 | Kaufman et al. |
| 2008/0171995 A1 | 7/2008 | Vitullo et al. |
| 2008/0177250 A1 | 7/2008 | Howlett et al. |
| 2009/0008393 A1 | 1/2009 | Howlett et al. |
| 2009/0062766 A1 | 3/2009 | Howlett et al. |
| 2010/0000040 A1 | 1/2010 | Shaw et al. |
| 2010/0049170 A1 | 2/2010 | Solomon et al. |
| 2010/0050351 A1 | 3/2010 | Colantonio et al. |
| 2010/0100056 A1 | 4/2010 | Cawthon et al. |
| 2010/0298770 A1 | 11/2010 | Rubinstein et al. |
| 2011/0046603 A1 | 2/2011 | Felsovalyi et al. |
| 2011/0054440 A1 | 3/2011 | Lewis |
| 2011/0213341 A1 | 9/2011 | Solomon et al. |
| 2011/0264037 A1 | 10/2011 | Foshee et al. |
| 2012/0039764 A1 | 2/2012 | Solomon et al. |
| 2012/0109073 A1 | 5/2012 | Anderson et al. |
| 2012/0111368 A1 | 5/2012 | Rahimy et al. |
| 2012/0123386 A1 | 5/2012 | Tsals |
| 2012/0265163 A1 | 10/2012 | Cheng et al. |
| 2012/0302997 A1 | 11/2012 | Gardner et al. |
| 2013/0085474 A1 | 4/2013 | Charles et al. |
| 2013/0171030 A1 | 7/2013 | Ferlic et al. |
| 2013/0197485 A1 | 8/2013 | Gardner et al. |
| 2013/0338644 A1 | 12/2013 | Solomon et al. |
| 2014/0052074 A1 | 2/2014 | Tekeste |
| 2014/0135706 A1 | 5/2014 | Rubinstein et al. |
| 2014/0148781 A1 | 5/2014 | Tekeste |
| 2014/0150832 A1 | 6/2014 | Rogers et al. |
| 2014/0228772 A1 | 8/2014 | Ward et al. |
| 2014/0364803 A1 | 12/2014 | Rubinstein et al. |
| 2015/0094659 A1 | 4/2015 | Schraga |
| 2015/0094666 A1 | 4/2015 | Bates et al. |
| 2015/0182704 A1 | 7/2015 | Chevallier |
| 2015/0190580 A1 | 7/2015 | Imai et al. |
| 2015/0190586 A1 | 7/2015 | Takemoto |
| 2015/0374968 A1 | 12/2015 | Solomon et al. |
| 2016/0045629 A1 | 2/2016 | Gardner et al. |
| 2016/0067422 A1 | 3/2016 | Davis et al. |
| 2016/0158520 A1 | 6/2016 | Ma et al. |
| 2017/0203092 A1 | 7/2017 | Ryan et al. |
| 2018/0085568 A1 | 3/2018 | Drmanovic |
| 2018/0200145 A1 | 7/2018 | Sanders et al. |
| 2018/0200500 A1 | 7/2018 | Ziebol et al. |
| 2018/0237190 A1 | 8/2018 | Iwasaki |
| 2018/0243547 A1 | 8/2018 | Fox et al. |
| 2018/0256879 A1 | 9/2018 | Chiu et al. |
| 2018/0256883 A1 | 9/2018 | Follman et al. |
| 2019/0151643 A1 | 5/2019 | Alpert |
| 2019/0232039 A1 | 8/2019 | Erekovcanski et al. |
| 2019/0234540 A1 | 8/2019 | Marici et al. |
| 2019/0308006 A1 | 10/2019 | Erekovcanski et al. |
| 2019/0351212 A1 | 11/2019 | Dudar et al. |
| 2020/0238070 A1 | 7/2020 | Ryan |
| 2021/0100996 A1 | 4/2021 | Wijesuriya et al. |
| 2021/0187267 A1 | 6/2021 | Jiang |
| 2022/0273931 A1 | 9/2022 | Jiang et al. |
| 2023/0080687 A1 | 3/2023 | Ryan |

FOREIGN PATENT DOCUMENTS

| | | |
|---|---|---|
| CN | 1322119 A | 11/2001 |
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103079610 A | 5/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 2606930 A1 | 6/2013 |
| EP | 2585146 B1 | 3/2017 |
| EP | 2832391 B1 | 1/2018 |
| EP | 3275490 A1 | 1/2018 |

(56) References Cited

FOREIGN PATENT DOCUMENTS

| | | |
|---|---|---|
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2012522593 A | 9/2012 |
| JP | 2013529973 A | 7/2013 |
| JP | 2015517377 A | 6/2015 |
| JP | 2016511119 A | 4/2016 |
| JP | 2016104214 A | 6/2016 |
| MX | 2013/000081 | 3/2013 |
| MX | 349289 B | 7/2017 |
| WO | 0019878 | 4/2000 |
| WO | 200024442 A1 | 5/2000 |
| WO | 200224551 A1 | 3/2002 |
| WO | 2011066586 A1 | 6/2011 |
| WO | 2012/013587 A1 | 2/2012 |
| WO | 2013046857 A1 | 4/2013 |
| WO | 2014159346 A1 | 10/2014 |
| WO | 2015121602 A1 | 8/2015 |
| WO | 2015127285 A1 | 8/2015 |
| WO | 2015174953 A1 | 11/2015 |
| WO | 2017087400 A1 | 5/2017 |
| WO | 2017095373 A1 | 6/2017 |
| WO | 2016158144 A1 | 1/2018 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |
| WO | 2019212637 A1 | 11/2019 |
| WO | 2020112767 A1 | 6/2020 |

OTHER PUBLICATIONS

PCT Invitation to Pay Additional Fees in PCT/US2021/019546, dated Jun. 15, 2021, 17 pages.
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/027220 dated Jul. 21, 2021, 15 pages.
PCT Invitation to Pay Additional Fees in PCT/US2021/027219, dated Jul. 22, 2021, 15 pages.
Non-Final Office Action in U.S. Appl. No. 16/774,853 dated Feb. 1, 2022, 12 pages.
"PCT International Search Report and Written Opinion in PCT/US2021/027219 dated Oct. 22, 2021, 22 pages".
Final Office Action in U.S. Appl. No. 16/253,683, dated Dec. 23, 2020, 9 pages.
Final Office Action in U.S. Appl. No. 16/254,747, dated Jan. 22, 2021, 15 pages.
PCT International Search Report in PCT/US2019/015789, dated Apr. 16, 2019, 12 pages.
Non-Final Office Action in U.S. Appl. No. 16/378,015, dated Mar. 30, 2021, 10 pages.
Non-Final Office Action in U.S. Appl. No. 15/838,461 dated Jul. 24, 2020, 10 pages.
Non-Final Office Action in U.S. Appl. No. 16/253,683, dated Jun. 26, 2020, 9 pages.
Non-Final Office Action in U.S. Appl. No. 16/254,747, dated Aug. 20, 2020, 14 pages.
Non-Final Office Action in U.S. Appl. No. 16/378,015, dated Oct. 30, 2020, 18 pages.
PCT International Search Report and Written Opinion in PCT/US2017/065956 dated Mar. 5, 2018, 14 pages.
PCT International Search Report and Written Opinion in PCT/US2019/015096 dated Mar. 21, 2019, 12 pages.
PCT International Search Report and Written Opinion in PCT/US2019/015100 dated Apr. 10, 2019, 10 pages.
PCT International Search Report and Written Opinion in PCT/US2019/026482 dated Jul. 30, 2019, 13 pages.
PCT International Search Report and Written Opinion in PCT/US2020/015535 dated May 4, 2020, 13 pages.
PCT International Search Report and Written Opinion in PCT/US2020/041097 dated Oct. 28, 2020, 18 pages.
PCT International Search Report and Written Opinion in PCT/US2020/041311 dated Sep. 30, 2020, 16 pages.
PCT International Search Report and Written Opinion in PCT/US2020/041312 dated Oct. 19, 2020, 11 pages.
PCT International Search Report and Written Opinion in PCT/US2020/044942 dated Oct. 16, 2020, 15 pages.
PCT International Search Report and Written Opinion in PCT/US2020/044951 dated Oct. 14, 2020, 14 pages.
PCT International Search Report and Written Opinion in PCT/US2020/057611 dated Feb. 5, 2021, 11 pages.
PCT International Search Report and Written Opinion in PCT/US2020/065229 dated Mar. 29, 2021, 11 pages.

DISINFECTION CAP

TECHNICAL FIELD

The present disclosure relates to disinfection cap devices for disinfecting corresponding medical connectors. The present disclosure generally relates to a device for disinfecting and sterilizing access ports of medical connectors having a fitting. Generally, exemplary embodiments of the present disclosure relate to the fields of threaded or interlocking fittings, including medical caps and medical disinfection caps, and in particular caps and/or disinfection caps for uses with threaded fluid connectors. One or more exemplary embodiments of the present disclosure relate to male disinfection cap devices for disinfecting male threaded luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hub, port, or valve upon connection to the VAD to deliver the fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

The need to protect female and male luer connectors to reduce central line-associated bloodstream infections (CLABSI) and peripheral line-associated bloodstream infection (PLABSI) has been rising. Intravenous gravity sets and threaded male luer connections on syringes are subject to contamination when not protected properly. Currently when IV connectors are disconnected from central lines or peripheral lines to temporarily discontinue infusion, nurses often loop the male luer connector to a Y-site needle-free connector or wrap the male luer connector in a piece of Isopropyl Alcohol ("IPA") impregnated wipe or cloth. However such protection is very weak and does not protect the luer from touch contamination properly. Male disinfection caps have become the state of art disinfection and protection device to disinfect and create a physical barrier on male luer connector to prevent microbial growth.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded male luer connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Disinfectants typically have a threshold limit for systemic exposure for infusion into blood stream due to biotoxicity of the disinfectants at high dosage. Thus, there is a need for a disinfection device capable of blocking the lumen of open luers to facilitate the mitigation of such disinfectant ingress into connectors, thereby reducing risk of the disinfectant entering the blood stream. There is a need for a mechanism to prevent disinfectant from entering the lumen and fluid path while providing effective disinfection of the surrounding connector or fitting.

SUMMARY

A first aspect of the present disclosure relates to a disinfection cap having a housing comprising a top wall, a cylindrical sidewall, and an open bottom formed by the cylindrical sidewall. The cylindrical sidewall has an inner surface defining a cavity. The open bottom has an opening to the cavity for receiving a hub of a luer connector.

A blockage feature is disposed within the cavity. The blockage feature is configured as a cylindrical protrusion being disposed on the top wall of the housing. The cylindrical protrusion fluidly blocks the hub of the luer connector. A fluid releasably retained within a depressible open cell foam structure is disposed within the cavity. The hub of said luer connector is received within said inner surface of said cavity.

In one or more embodiments, the cavity extends essentially from an inner surface of said top wall toward said open bottom of said housing.

In one or more embodiments, the cylindrical protrusion is non-removably disposed on the top wall of the housing.

In one or more embodiments the open cell foam structure is disposed against the top wall. In one or more embodiments, the open cell foam structure has a hollow cylindrical shape configured to fit around the cylindrical protrusion.

In one or more embodiments, the cylindrical protrusion further includes an upper portion and a lower portion, the upper portion having a diameter equal to the top wall, the lower portion having a diameter smaller than the upper portion, the lower portion configured to fluidly block the hub of the luer connector.

In one or more embodiments, the open cell foam structure is disposed against a bottom surface of the upper portion of the cylindrical protrusion. The open cell foam structure has a hollow cylindrical shape configured to fit around the lower portion of the cylindrical protrusion.

In one or more embodiments, the second depressible open cell foam is disposed between the upper portion of the cylindrical protrusion and the top wall of the cavity. The second open cell foam structure releasably retains a fluid.

In one or more embodiments, the disinfection cap further includes at least one thread on the outer surface of the housing. The at least one thread being sufficient to interlock with a mating feature of the luer connector.

In one or more embodiments, the hub is secured within the inner surface of the cavity by interlocking at least a portion of the at least one thread with a mating feature on the hub of the luer connector.

In one or more embodiments, the inner surface of the cavity is secured by an interference fit with the hub of the luer connector.

In one or more embodiments the fluid is selected from a group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

A second aspect of the present disclosure relates to a disinfection cap having a housing comprising a top wall having an aperture extending partially into the housing, a cylindrical sidewall having an inner surface defining a cavity, an open bottom formed by the cylindrical sidewall with an opening to the cavity within the housing for receiving a hub of a luer connector. An umbrella stopper includes a stem, the stem at least partially disposed into the aperture of the top wall. The umbrella stopper further includes a fanned barrier configured as a blockage feature for fluidly blocking a hub of a medical device. The fanned barrier creates a liquid tight seal with the inner surface of the sidewall. A fluid is releasably retained within the cavity and the fanned barrier of the umbrella stopper. The hub of the luer connector is received within the inner surface of the cavity. When the fanned barrier deforms when moved against the hub, fluid is released.

In one or more embodiments, the umbrella stopper further includes a rounded or chamfered end, the rounded or chamfered end is configured to fluidly block the hub of the luer connector. In one or more embodiments the fanned barrier is at a right angle to the stem. In one or more embodiments the fanned barrier is at an obtuse angle to the stem.

A third aspect of the present disclosure relates to a disinfection cap having a housing comprising top wall, a cylindrical sidewall having an inner surface defining a cavity, an open bottom formed by a cylindrical sidewall with an opening to the cavity within said housing for receiving a hub of a luer connector. A blockage feature is disposed within the cavity, the blockage feature being configured as a plurality of hydrophilic bristles. The hydrophilic bristles are disposed on the top wall of the housing, the hydrophilic bristles fluidly blocking the hub of the luer connector; and a fluid releasably retained within the hydrophilic bristles. The hub of said luer connector is received within said inner surface of said cavity.

In one or more embodiments the disinfection cap further includes a movable conical stopper, the conical stopper comprising a top portion and a bottom portion, the top portion including a flange having a diameter less than the diameter of the cavity. The top portion further includes a lumen extending therethrough. The cavity includes a protrusion configured as a secondary blockage feature by which the protrusion blocks the hub of the luer connector.

A fourth aspect of the present disclosure relates to a disinfection cap having a housing comprising a top portion including a set of winged protrusions configured to receive a membrane or pouch, the membrane or pouching including a bulbous cavity for retaining a fluid and a fluid path fluidly connecting the bulbous cavity to a drain. The drain is disposed on a top surface of the top portion, the drain includes a conical cavity having a lumen disposed on a bottom surface of the conical cavity. The lumen is in fluid communication with a cavity defined by an inner sidewall of a bottom portion of the housing. At least two spines extend from the top surface into a center of the conical cavity, the at least two spines structurally securing a protrusion disposed within the cavity, the protrusion extending through the lumen. The protrusion is configured as blockage feature by which the lower portion has a diameter equal to or greater than the diameter of a hub of a medical device. An open bottom is formed by a cylindrical sidewall of the cavity with an opening to the cavity within said housing for receiving a hub of a luer connector.

In one or more embodiments, the hub of the luer connector is received within the inner surface of said cavity.

A fifth aspect of the present disclosure relates to a disinfection cap having a housing comprising an upper portion and an open bottom. The upper portion has an engagement surface disposed around a circumference of a top surface of the upper portion. The engagement surface is configured to receive a membrane or pouch, the membrane or pouch having a dome shape defining a bulbous cavity for retaining fluid. The open bottom is formed by a cylindrical sidewall of the cavity with an opening to the cavity for receiving a hub of a luer connector. At least two vents or slits are disposed through the top surface of the upper portion, the at least two vents or slits are in fluid communication with the bulbous cavity of the upper portion and the cavity. The hub of the luer connector is received within an inner surface of the cavity. The bulbous cavity may be depressed or collapsed onto the top surface of the upper portion, thereby releasing fluid into the at least two vents or slits.

In one or more embodiments the hub of the luer connector abuts a top wall of the cavity, the top wall fluidly sealing the hub of the luer connector.

DETAILED DESCRIPTION

Figure 1:
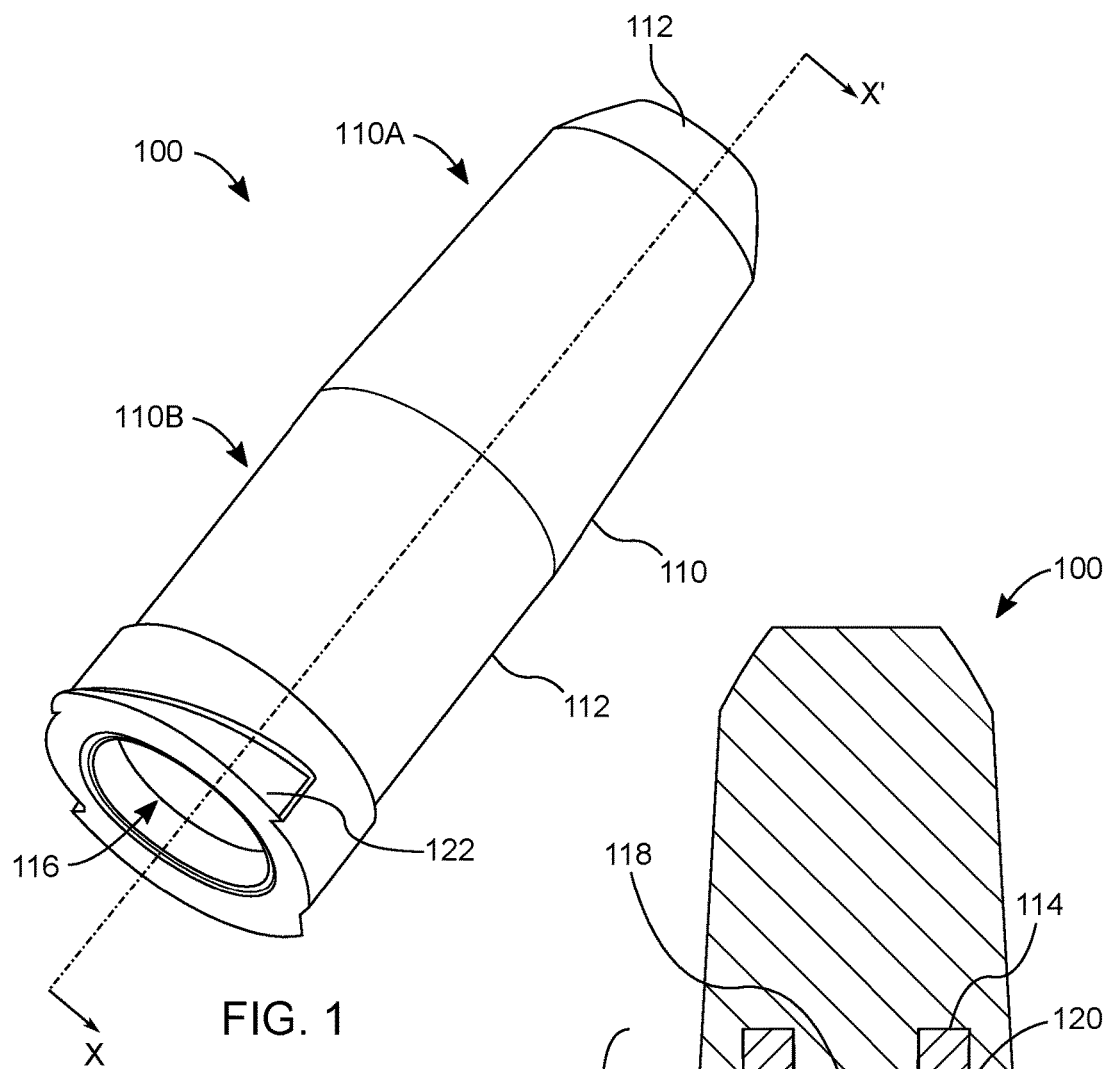
FIG. 1 illustrates a perspective view of a disinfection cap according to an exemplary first embodiment of the disclosure.

Embodiments of the disclosure pertain to a disinfection cap for connection to and disinfection of a medical connector, including threaded connections. In one or more embodiments, the medical connector is a needless connector or a luer connector. The disclosure aims to provide a mechanism to prevent disinfectant from entering the fluid path of the medical connector while providing for effective disinfection for the hub and surrounding periphery of the medical connector.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of and interlocking tubes, slightly tapered to hold together with just a simple pressure/twist fit. Luer connectors can optionally include an additional outer rim of threading, allowing them to be more secure. The Luer connector end is generally associated with a flush syringe and can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term "Luer connector" refers to a luer connector or a female luer connector.

As used herein, the term "medical device" refers to common medical devices having threaded or interlocking connections, the connections having corresponding mating elements. By way of example but not limitation, a syringe may have a threaded connection which releasably interlocks with a secondary medical device such as a luer connection of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

Embodiments of the disinfection cap of the present disclosure comprise a housing having a top wall defining a closed end, a substantially cylindrical sidewall having an inner surface defining a cavity, an open end formed by said cylindrical sidewall with an opening to the cavity within said housing for receiving a hub of a threaded connection, an at least one thread on an exterior surface of the cylindrical sidewall that is sufficient to interlock with a mating feature of said threaded connection, a blockage feature disposed within the cavity, and a disinfectant or antimicrobial agent retained within the cavity. Embodiments of the disinfection cap disclose the at least one thread of the disinfection cap engaging the mating feature of the threaded connection, and more specifically a luer connection. The blockage feature is configured to prevent disinfectant ingress into a fluid path of the hub of the luer connection. In one or more embodiments, the exterior surface of the housing at the open end of the disinfection cap includes a peripheral ledge extending radially outward from the open end defining an end face and an engagement surface for a peelable seal and/or septum for maintaining sterility of the cavity. The peelable seal reduces or prevents contamination of the cavity during shipping and storage of the disinfection cap. The peelable seal is generally kept in the closed position until just prior to an injection and/or aspiration procedure, at which time the peelable seal is removed. The removable seal minimizes entry of potential particulate hazard and also provides a substantially impermeable enclosure for the cavity prior to use of the disinfection cap. The removable seal provides a sufficient seal at a range of temperatures, pressures, and humidity levels.

The disinfection cap provides a mechanical barrier for connectors and contains a disinfectant fluid or an antimicrobial agent (hereinafter "fluid"). The disinfection cap of the present disclosure allows the practitioner to streamline the disinfecting process. The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In particular, the practitioner may disinfect the luer connector in a single motion by inserting or threading the disinfection cap onto the luer connector of the medical device which causes the blockage feature to prevent fluid ingress into the fluid path of the luer connector, while the hub of the luer connector simultaneously causes the release of the fluid allowing for disinfection of the luer connector hub and its periphery. The disinfection cap may then be removed by removing or unthreading the disinfection cap from the luer connector of the medical device and inserting or threading onto the luer connector, by way of example, a Y-site connection or a luer connector.

In an exemplary implementation of the embodiments of present disclosure, the disinfection cap includes integrated threads or tabs, and other features in any and all combinations allowing it to interface with a threaded fitting of a medical device. In preferred embodiments, the disinfection cap interfaces with a Luer fitting. Exemplary configurations for couplers, fittings, ports and adapters may include commercially available luer locks, luer slip ports, locking ports, threaded connections, interlocking connection or generally other common medical device fitting known in the art.

Referring now to the drawings, wherein like reference numerals designate identical or corresponding parts throughout the several views, embodiments of the present disclosure are described as follows.

Figure 2:
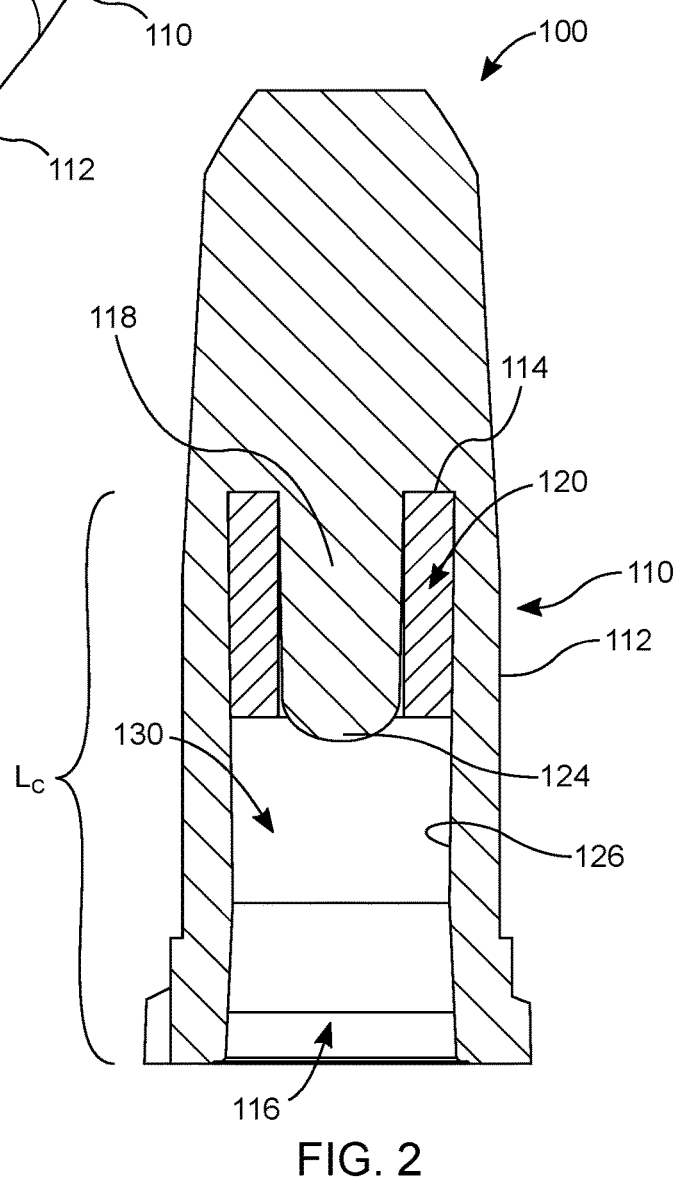
FIG. 2 illustrates a cross sectional view of the disinfection cap along the axis X-X' in accordance with a first embodiment of the present disclosure.

As depicted in FIGS. 1 and 2, a first aspect of the present disclosure relates to a disinfection cap 100 including a housing 110 having an upper portion 110A and a lower portion 110B. In one or more embodiments, the lower portion 110B is substantially cylindrical having a cylindrical housing 112. In further embodiments, the lower portion 110B may have tapered lower portion. The upper portion 110A of the housing has an inwardly tapered sidewall. In further embodiments, the upper portion 110A and lower portion 110B have a substantially cylindrical sidewall. In one or more embodiments, an inner surface 126 of the lower portion 110B of the housing 110 defines a cavity 130 having open bottom 116 for receiving a hub of a luer connector. In one embodiment, upper portion 110A is integrally formed with the lower portion 110B while further embodiments are non-removably or removably assembled with a threaded connection, press-fit connection, adhesive connection or a combination thereof.

In one or more embodiments, the cavity 130 can be configured to facilitate a loose fit between the cavity 130 and the hub of the luer connector, wherein the disinfection cap 100 is secured by an at least one thread 122 or set of tabs included on the outer surface of the cylindrical housing 112. The at least one thread 122 disposed on the outer surface of the cylindrical housing 112 is sized and have a thread pattern that will engage with a standard ISO-2 type of fitting. The loose fit allows for fluid to flow around the hub of the luer connector. In further embodiments, the cavity 130 can be configured in a Luer Slip fitting to facilitate an interference fit between the cavity 130 and the hub of the luer connector. The interference fit can be configured to be sufficiently strong enough to not require a threaded connection or the at least one thread 122 in removably securing the cavity 130 to the luer connector.

In one or more embodiments, when the hub of the luer connector is received within the inner surface 126 of the cavity 130, the hub is secured within the cavity 130 of the disinfection cap 100 by interlocking at least a portion of the at least one thread 122 with a mating feature on the hub of the luer connector. In one or more embodiments, the at least one thread 122 can include an inclined thread pattern. In one or more embodiments, the at least one thread 122 can include a helical-shaped thread pattern. Such connectors are generally and commonly used as catheter and other fluid-tight protective connectors in medical applications. In some embodiments, the disinfectant cap 100 provides a protective cover for a luer connector when engaged with the connector when threads from the luer connector engage and form a releasable connection with at least one thread 122 of disinfection cap 100.

FIG. 2 depicts a cross-sectional view of the disinfection cap 100 along an X-X' plane as shown in FIG. 1. As depicted in FIG. 2, cavity 130 of the housing 110 extends a length $L_C$ of the total length of the housing 110 from the open bottom 116 to a top wall 114, the cavity 130 having a substantially cylindrical shape. From the top wall 114 extends a protrusion 118 configured as a blockage feature for a lumen extending through the hub of the luer connector of the medical device. The protrusion 118 in the preferred embodiment has a substantially cylindrical shape and is uniformly connected to the top wall 114. The diameter of protrusion 118 is sized and configured to fluidly block the lumen of the luer connector. In one or more embodiments, the protrusion 118 has a substantially conical shape. In one or more embodiments, the end 124 of the protrusion 118 is rounded or chamfered to aid in inserting the protrusion 118 into the lumen of the luer connector.

An open cell foam structure 120 for absorbing and retaining fluid can be disposed against the top wall 114. In the preferred embodiment, the open cell foam structure 120 having a hollow cylindrical shape, configured to fit around the protrusion 118, not extending beyond the protrusion 118. The open cell foam structure 120 is compressible in both horizontal and vertical directions, allowing the open cell foam structure 120 to create an interference fit with the inner surface 126 of the cavity 130. The open cell foam allows for fluid to be excreted as the open cell foam structure 120 is compressed. As the disinfection cap 100 is threaded or pushed against the luer connector, the lumen of the luer connector is fluidly sealed and blocked by the protrusion 118 while the hub of the luer connector compresses the open cell foam structure 120, releasing the fluid which disinfects the hub and the periphery of the luer connector. In the preferred embodiment, the open cell foam structure 120 can be neoprene, polyurethane, natural rubber, or medical-grade open cell foam having low or zero cytotoxicity ratings suitable for sterilization.

Figure 3A:
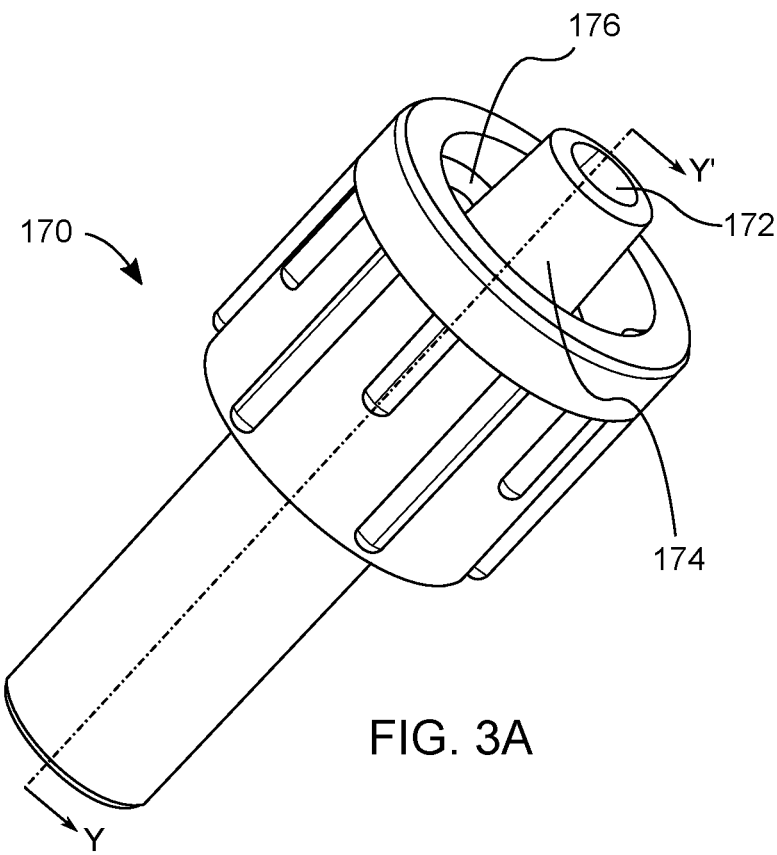
FIG. 3A illustrates a perspective view of a threaded connection in accordance with a first embodiment of the present disclosure.
Figure 3B:
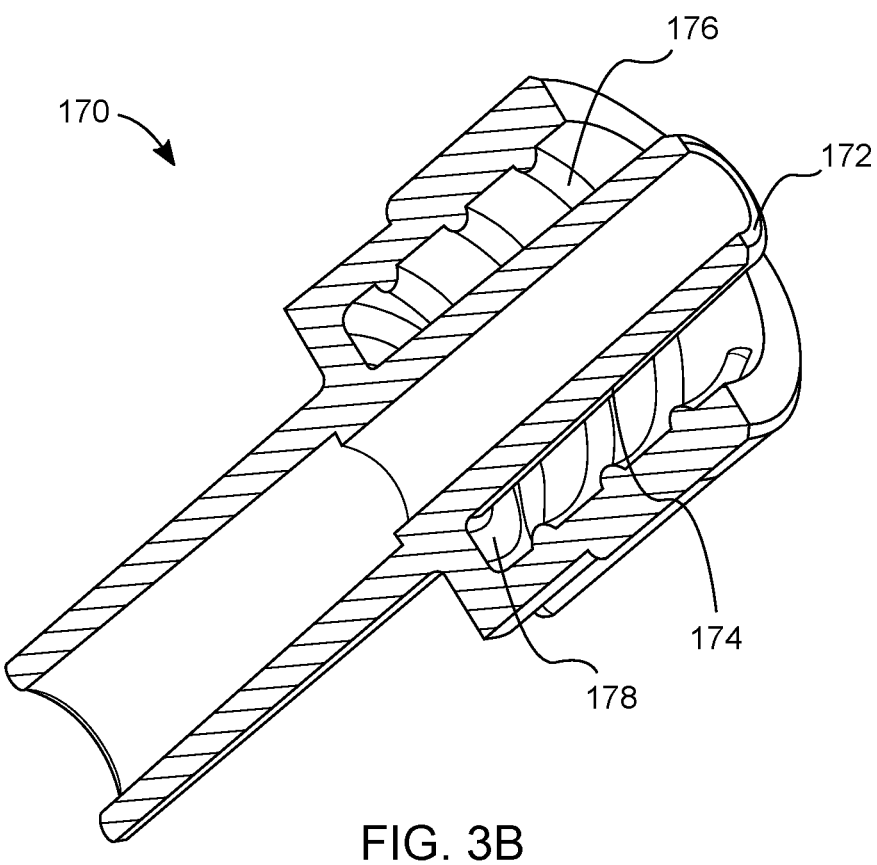
FIG. 3B illustrates a perspective view of the threaded connection along the axis Y-Y' in accordance with a first embodiment of the present disclosure.
Figure 4A:
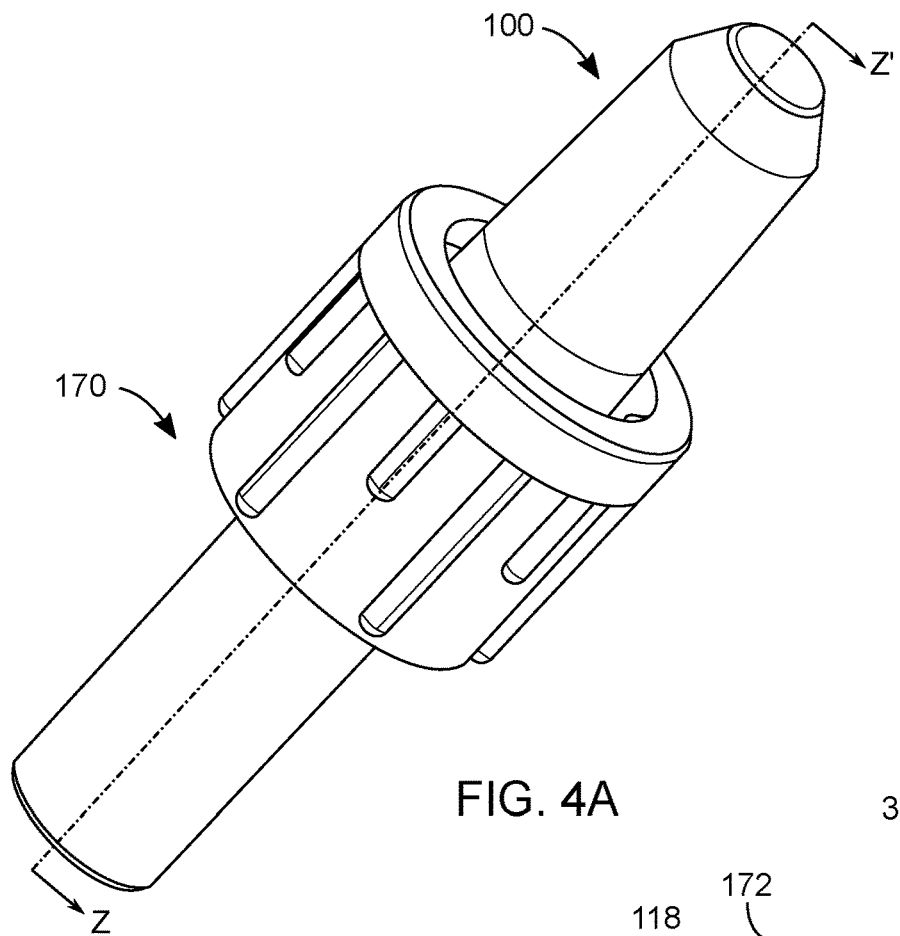
FIG. 4A illustrates a perspective view of the disinfection cap in accordance with the first embodiment of the present disclosure.
Figure 4B:
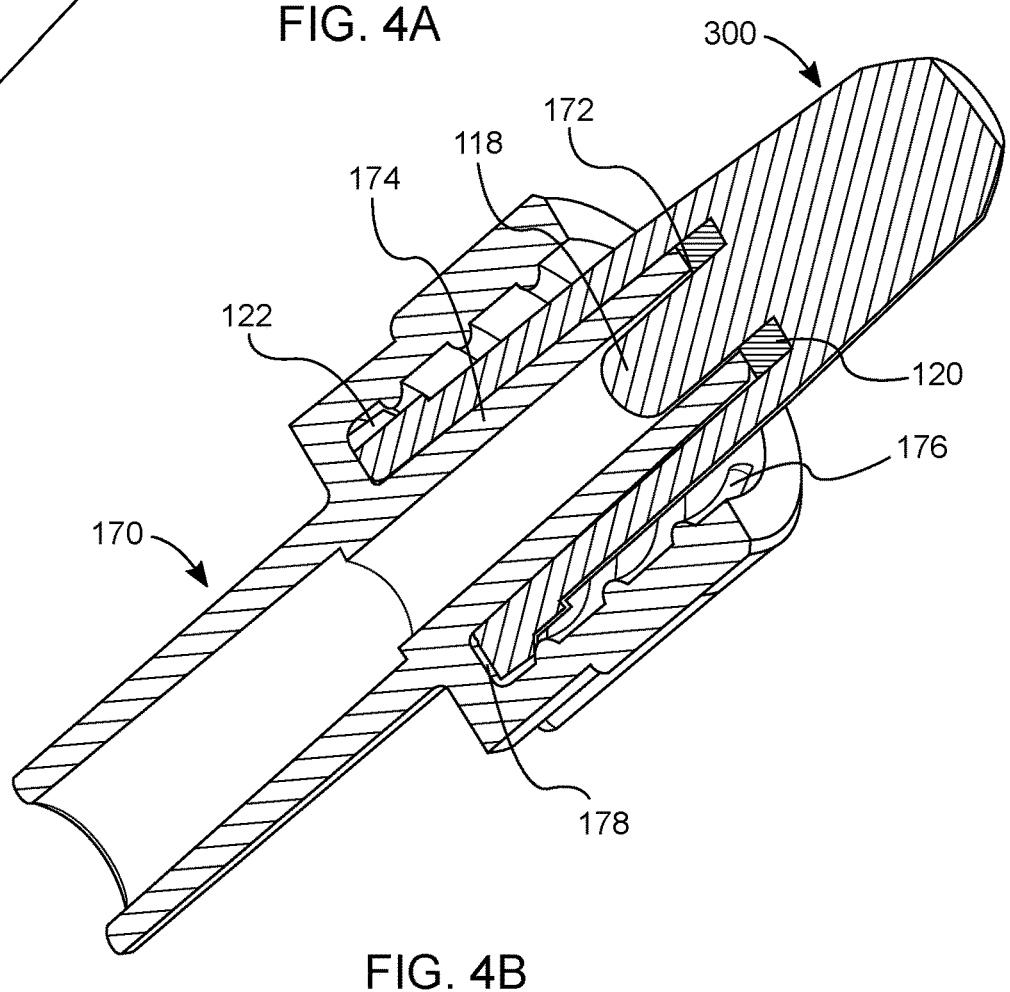
FIG. 4B illustrates a perspective view of the disinfection cap along the axis Z-Z' in accordance with the first embodiment of the present disclosure.

An exemplary luer connector 170 is depicted in FIGS. 3A and 3B, with FIG. 3A illustrating a cross-section along plane Y-Y'. The luer connector 170 includes a lumen 172 disposed through a hub 174 having a conical surface, a mating feature having at least one thread 176, and a mating surface 178 disposed at the bottom of the hub 174. FIGS. 4A and 4B depict the disinfection cap 100 fully inserted into the luer connector 170, with FIG. 4B illustrating a cross-section along plane Z-Z'. As depicted, the at least one thread 122 of the disinfection cap 100 has fully engaged and releasably secured to the at least one thread 176 of the luer connector 170. In this position, an engagement surface of the disinfection cap 100 abuts the mating surface 178 of the luer connector 170. In this position, the hub 174 has fully depressed the open cell foam structure 120, thereby releasing the fluid contained within and disinfecting the hub 174 and the periphery of the luer connector 170 while the protrusion 118 of the disinfection cap 100 fluidly seals the lumen 172 of the luer connector 170, preventing fluid from entering the fluid path of the lumen 172 of the luer connector 170.

Further embodiments of the disinfection cap are contemplated having alternative blockage features. Exemplary disinfection caps include a housing having an upper portion and a lower portion. In one or more embodiments, the lower portion of the sidewall is substantially cylindrical having a cylindrical housing, while further embodiments may have tapered housing. The upper portion of the housing has an inwardly tapered sidewall, while further embodiments have a substantially cylindrical sidewall. In one or more embodiments, the inner surface of the lower portion of the housing defines a cavity having open bottom for receiving a hub of a luer connector.

In one or more embodiments, exemplary cavities can be configured to facilitate a loose fit between the cavity and the hub of the luer connector, wherein the exemplary disinfection cap is secured by an at least one thread or set of tabs included on the outer surface of the cylindrical housing. The loose fit allows for fluid to flow around the hub of the luer connector. In further embodiments, the exemplary cavity can be configured in a Luer Slip connection to facilitate an interference fit between the cavity and the hub of the luer connector. The interference fit can be configured to be sufficiently strong enough to not require a threaded connection or the at least one thread in removably securing the cavity to the luer connector.

In one or more embodiments, when the hub of the luer connector is received within the inner surface of the cavity, the hub is secured within the cavity of the disinfection cap by interlocking at least a portion of the at least one thread with a mating feature on the hub of the luer connector. In one or more embodiments, the at least one thread can include an inclined thread pattern. In one or more embodiments, the at least one thread can include a helical-shaped thread pattern. Such connectors are generally and commonly used as catheter and other fluid-tight protective connectors in medical applications. In some embodiments, the disinfectant cap provides a protective cover for a luer connector when engaged with the connector when threads from the luer connector engage and form a releasable connection with at least one thread of the disinfection cap.

Figure 5A:
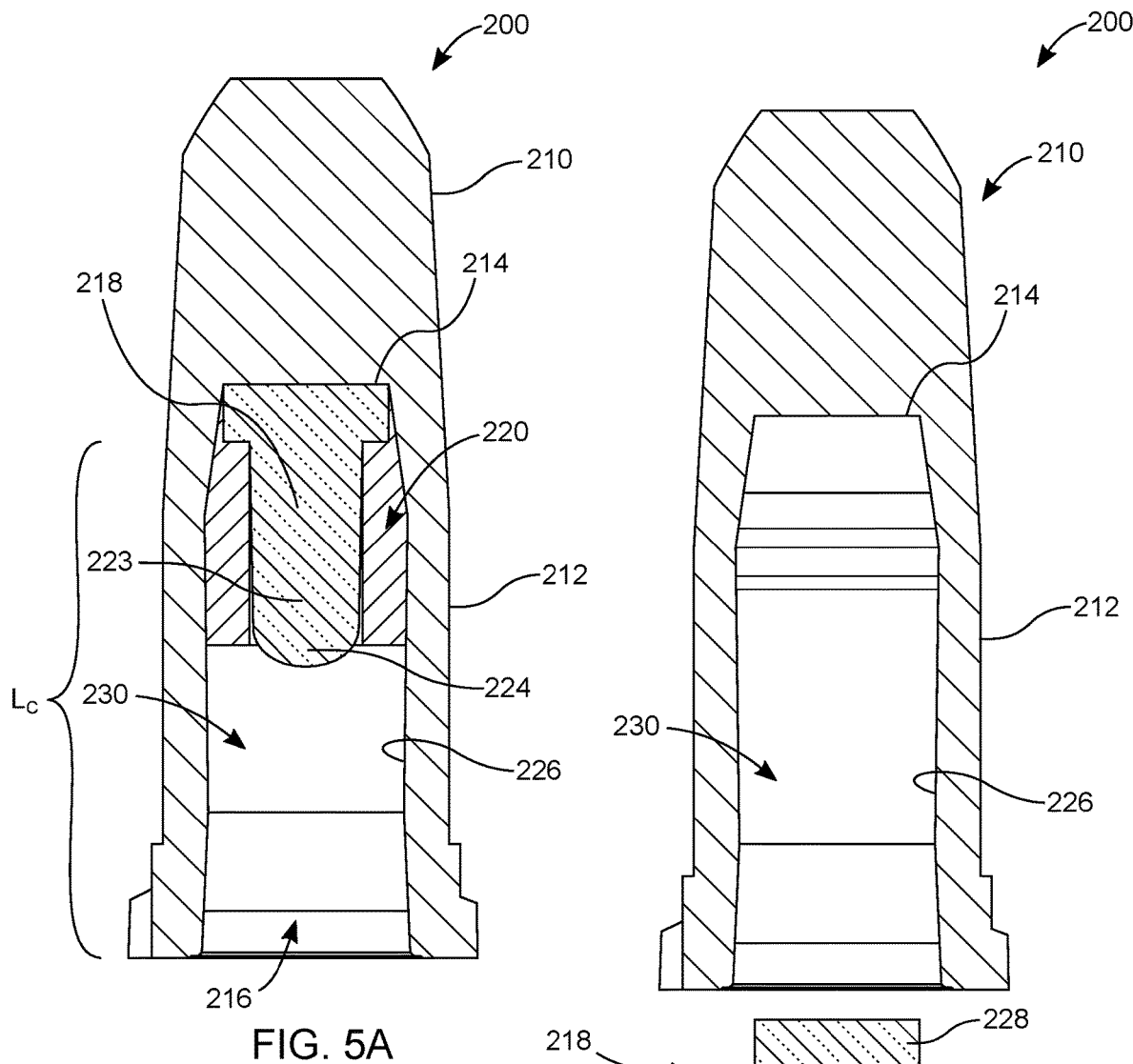
FIG. 5A illustrates a cross-sectional view of the disinfection cap in accordance with a second embodiment of the present disclosure.
Figure 5B:
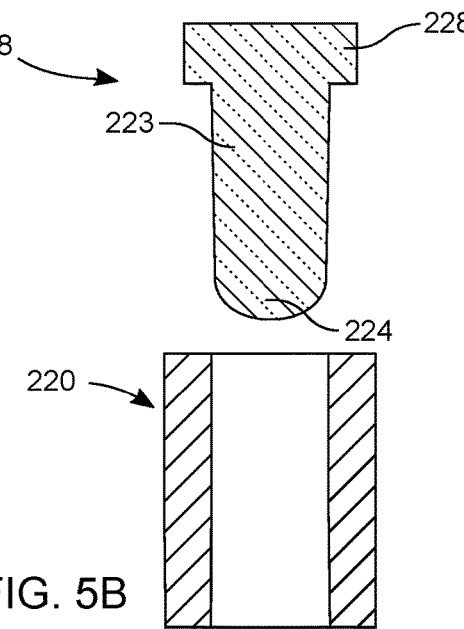
FIG. 5B illustrates an exploded cross-sectional view of the disinfection cap in accordance with a second embodiment of the present disclosure.

FIGS. 5A and 5B depict an exemplary disinfection cap 200 in accordance with a second embodiment of the present disclosure, with FIG. 5B depicting an exploded view of the exemplary disinfection cap 200 and FIGS. 5A and 5B depicting cross sections. The disinfection cap 200 includes a housing 210 having a lower portion with an inner surface 226 of the lower portion of the housing 210 defining a cavity 230 having open bottom 216 for receiving a hub of a luer connector.

The cavity 230 of the housing 210 extends a length $L_C$ of the total length of the housing 210 from the open bottom 216 to a top wall 214, the cavity 230 having a substantially cylindrical shape. A stopper 218 abuts the top wall 214, the stopper 218 being configured as a blockage feature for a lumen extending through the hub of the luer connector of the medical device.

The stopper 218 in the preferred embodiment has a substantially cylindrical shape, having an upper portion 228 and a lower portion 223, the upper portion 228 and the lower portion 223 being integrally formed. The upper portion 228 has a diameter equal to or greater than the top wall 214, creating an interference fit which removably retains the stopper within the cavity 230. The diameter of the lower portion 223 of the stopper 218 is sized and configured to fluidly block the lumen of the luer connector. In one or more embodiments, the lower portion 223 has a substantially conical shape. In one or more embodiments, the end 224 of the lower portion 223 is rounded or chamfered to aid in inserting the lower portion 223 into the lumen of the luer connector. The diameter of the upper portion 228 is greater than the diameter of the lower portion 223. In the preferred embodiment, the stopper 218 is bonded to the top wall 214 of the cavity 230 of the disinfection cap 200 by an interference connection, medical grade adhesive connection or a combination thereof. The stopper 218 may be rubber, TPE or plastic.

An open cell foam structure 220 for absorbing and retaining fluid can be disposed against a bottom surface of the upper portion 228 of the stopper 218. In the preferred embodiment, the open cell foam structure 220 has a hollow cylindrical shape, configured to fit around the lower portion 223 of the stopper 218, not extending beyond the lower portion 223. The open cell foam structure 220 is compressible in both horizontal and vertical directions, allowing the open cell foam structure 220 to create an interference fit with the inner surface 226 of the cavity 230. The open cell foam structure 220 allows for fluid to be excreted as the open cell foam structure 220 is compressed. As the disinfection cap 200 is threaded or pushed against the luer connector, the lumen of the luer connector is fluidly sealed and blocked by the stopper 218 while the hub of the luer connector compresses the open cell foam structure 220, releasing the fluid which disinfects the hub and the periphery of the luer connector. In the preferred embodiment, the open cell foam structure 220 can be neoprene, polyurethane, natural rubber, or medical-grade open cell foam having low or zero cytotoxicity ratings suitable for sterilization.

Figure 6:
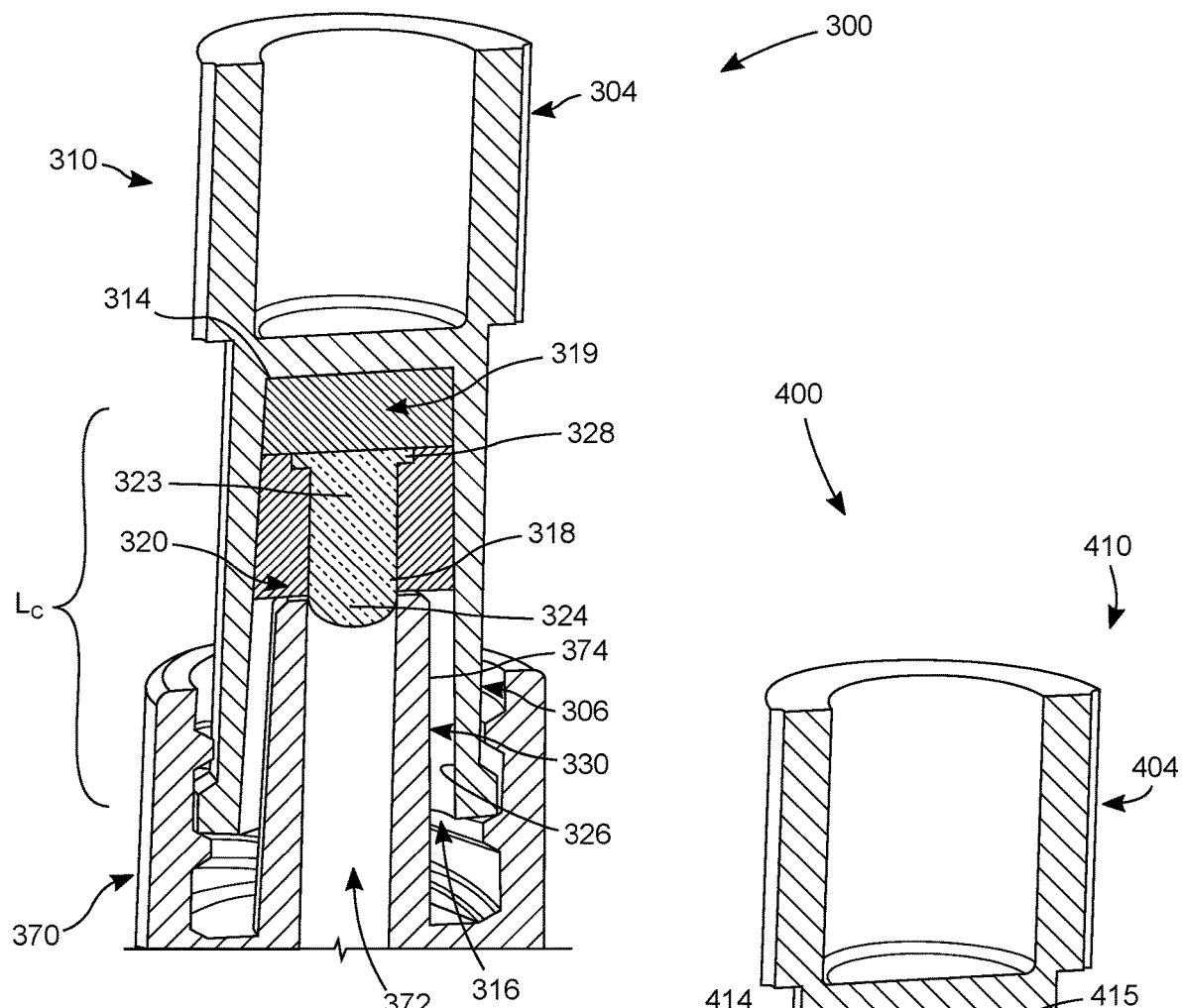
FIG. 6 illustrates a cross-sectional view of a disinfection cap in accordance with a third embodiment of the present disclosure.

FIG. 6 depicts an exemplary disinfection cap 300 in accordance with a third embodiment of the present disclosure. The disinfection cap 300 includes a housing 310 having an upper portion 304, a lower portion 306 and an inner surface 326 of the lower portion of the housing 310 defining a cavity 330 having open bottom 316 for receiving a hub of a luer connector. The upper portion 304 of the disinfection cap 300 has a larger diameter than the lower portion 306, the upper portion 304 serving as a gripping surface for a practitioner to manipulate the disinfection cap 300. In one embodiment, the upper portion 304 is integrally formed with the lower portion 306 while further embodiments is non-removably or removably assembled with a threaded connection, press-fit connection, adhesive connection or a combination thereof.

The cavity 330 of the housing 310 extends a length $L_C$ of the total length of the housing 310 from the open bottom 316 to a top wall 314, the cavity 330 having a substantially cylindrical shape. A first open cell foam structure 319 for absorbing and retaining fluid has a substantially cylindrical shape abutting the top wall 314.

A stopper 318 abuts a bottom surface of the first open cell foam structure 319, the stopper 318 being configured as a blockage feature for a lumen 372 extending through the hub 374 of the luer connector 370 of the medical device. The stopper 318 in the preferred embodiment has a substantially cylindrical shape, having an upper portion 328 and a lower portion 323, the upper portion 328 and the lower portion 323 being integrally formed. The upper portion 328 has a diameter equal to or greater than the top wall 314, creating an interference fit which removably retains the stopper within the cavity 330. The diameter of the lower portion 323 of the stopper 318 is sized and configured to fluidly block the lumen of the luer connector. In one or more embodiments the lower portion 323 can have a substantially conical shape. In one or more embodiments the end 324 of the lower portion 323 can be rounded or chamfered to aid in inserting the lower portion 323 into the lumen of the luer connector. The diameter of the upper portion 328 is greater than the diameter of the lower portion 323, and the diameter of the upper portion 328 is less than the diameter of the first open cell foam structure 319.

A second open cell foam structure 320 for absorbing and retaining fluid can abut the bottom surface of the first open cell foam structure 319. In the preferred embodiment, the open cell foam structure 220 has a hollow cylindrical shape, configured to fit around the lower portion 323 of the stopper 318, not extending beyond the lower portion 323. The first open cell foam structure 319 and the second open cell foam structure 320 have substantially the same outer diameters.

The first open cell foam structure 319 and the second open cell foam structure 320 are compressible in both horizontal and vertical directions, allowing the first open cell foam structure 319 and the second open cell foam structure 320 to create an interference fit with the inner surface 326 of the cavity 330. The first open cell foam structure 319 and the second open cell foam structure 320 allow for fluid to be excreted as the first open cell foam structure 319 and the second open cell foam structure 320 are compressed. As the disinfection cap 300 is threaded or pushed against the luer connector, the lumen of the luer connector is fluidly sealed and blocked by the stopper 318 while the hub of the luer connector compresses the first open cell foam structure 319 and the second open cell foam structure 320 releasing the fluid which disinfects the hub and the periphery of the luer connector. In the preferred embodiment, the first open cell foam structure 319 and the second open cell foam structure 320 can be neoprene, EPDM, Viton, polyurethane, natural rubber, or medical-grade open cell foam having low or zero cytotoxicity ratings suitable for sterilization.

Figure 7A:
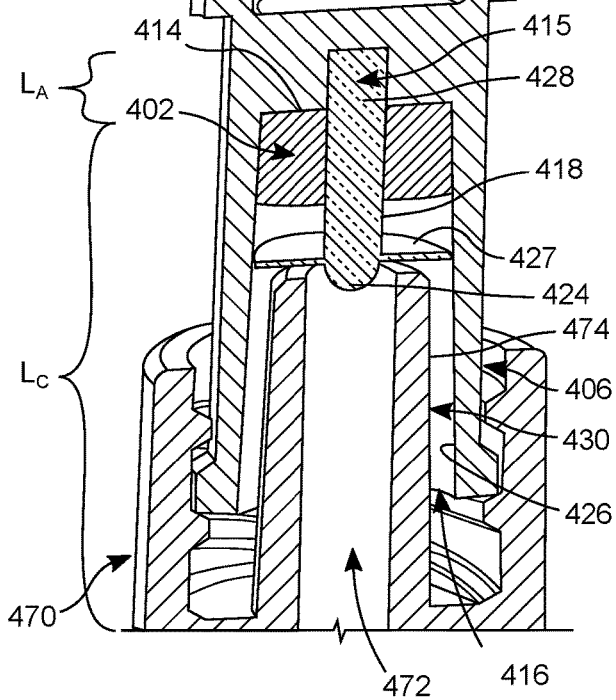
FIG. 7A illustrates a cross-sectional view of a disinfection cap in accordance with a fourth embodiment of the present disclosure.
Figure 7B:
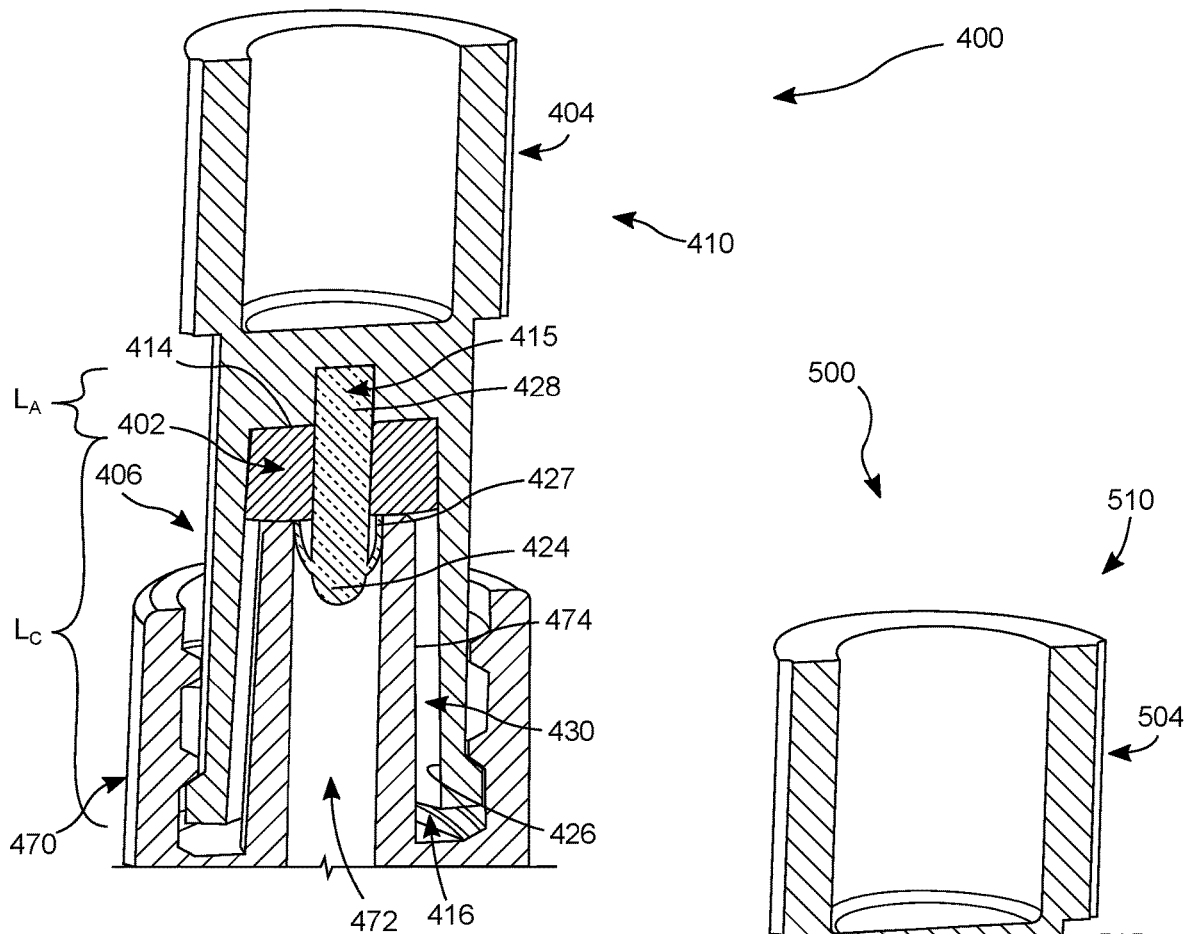
FIG. 7B illustrates a cross-sectional view of a disinfection cap in accordance with the fourth embodiment of the present disclosure.

FIGS. 7A and 7B depict an exemplary disinfection cap 400 in accordance with a fourth embodiment of the present disclosure. The disinfection cap 400 includes a housing 410 having an upper portion 404, a lower portion 406 and an inner surface 426 of the lower portion of the housing 410 defining a cavity 430 having open bottom 416 for receiving a hub of a luer connector. The upper portion 404 of the disinfection cap 400 has a larger diameter than the lower portion 406, the upper portion 404 serving as a gripping surface for a practitioner to manipulate the disinfection cap 400. In one embodiment, the upper portion 404 is integrally formed with the lower portion 406 while further embodiments are non-removably or removably assembled with a threaded connection, press-fit connection, adhesive connection or a combination thereof.

The cavity 430 of the housing 410 extends a length $L_C$ of the total length of the housing 410 from the open bottom 416 to a top wall 414, the cavity 430 having a substantially cylindrical shape. The top wall 414 further includes an aperture 415 extending a length LA into the housing 410. The aperture 415 extends towards the upper portion 404.

A stem 428 of an umbrella stopper 418 is at least partially disposed into the aperture 415. The stem 428 may be integrally formed into the aperture 415. In one or more embodiments, the stem 428 may be non-removably or removably assembled with a threaded connection, press-fit connection, adhesive connection or a combination thereof. The umbrella stopper 418 further includes a fanned barrier 427, wherein the umbrella stopper 418 and more specifically the fanned barrier 427 are configured as a blockage feature for a lumen 472 extending through the hub 474 of the luer connector 470 of the medical device. The fanned barrier 427 of the umbrella stopper 418 creates a liquid tight seal with the inner surface 426 of the cavity 430. The diameter of the fanned barrier 427 being essentially equal to the diameter of the cavity 430. In one or more embodiments an end 424 of the stem 428 can be rounded or chamfered to aid in inserting the stem 428 into the lumen 472 of the luer connector 470.

A fluid is disposed within a chamber defined by the fanned barrier 427 and an upper portion of the cavity 430. As the disinfection cap 400 is threaded or pushed against the luer connector, the fanned barrier 427 elastically deforms into the lumen 472, creating a liquid tight seal while the elastic deformation of the fanned barrier 427 interrupts the liquid tight seal of the fanned barrier 427 and the cavity 430, releasing the fluid which disinfects the hub and the periphery of the luer connector. In the preferred embodiment, the fanned barrier 427 can be made of a deformable elastomeric material such as rubber or TPE.

Figure 8A:
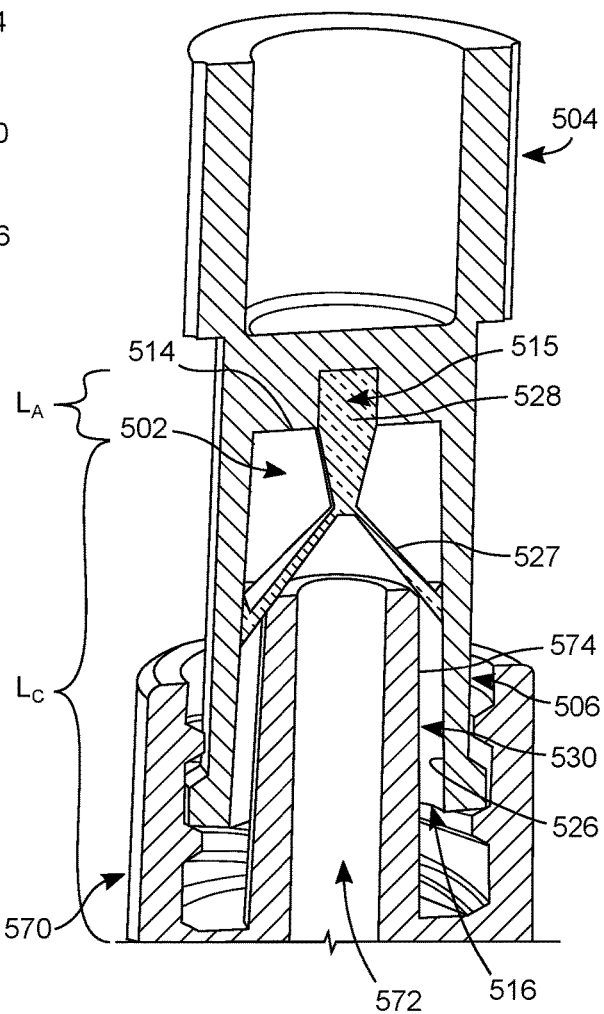
FIG. 8A illustrates a cross-sectional view of a disinfection cap in accordance with a fifth embodiment of the present disclosure.
Figure 8B:
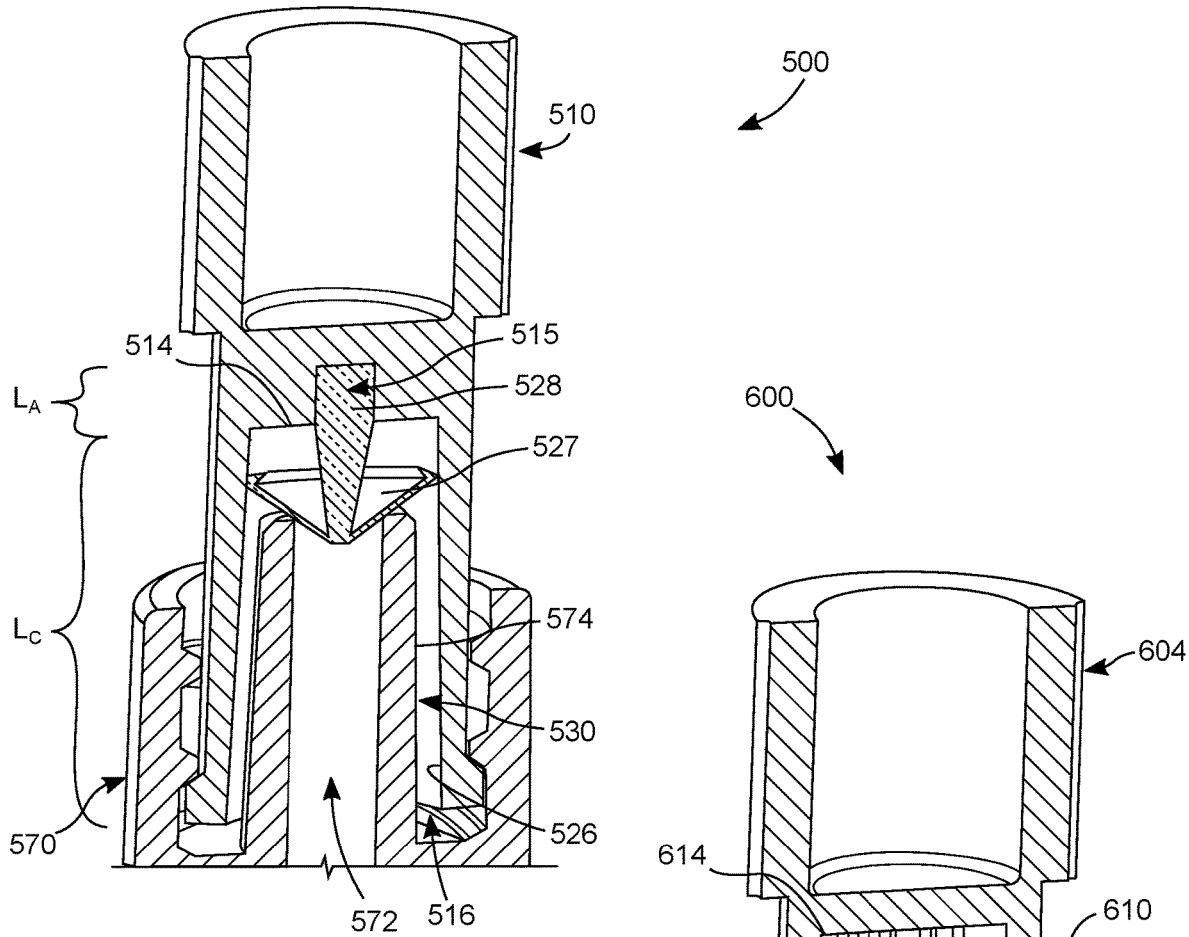
FIG. 8B illustrates a cross-sectional view of a disinfection cap in accordance with the fifth embodiment of the present disclosure.

FIGS. 8A and 8B depict an exemplary disinfection cap 500 in accordance with a fifth embodiment of the present disclosure. The disinfection cap 500 includes a housing 510 having an upper portion 504, a lower portion 506 and an inner surface 526 of the lower portion 506 of the housing 510 defining a cavity 530 having open bottom 516 for receiving a hub of a luer connector. The upper portion 504 of the disinfection cap 500 has a larger diameter than the lower portion 506, the upper portion 504 serving as a gripping surface for a practitioner to manipulate the disinfection cap 500. In one embodiment, the upper portion 504 is integrally formed with the lower portion 506 while further embodiments may be non-removably or removably assembled with a threaded connection, press-fit connection, adhesive connection or a combination thereof.

The cavity 530 of the housing 510 extends a length $L_C$ of the total length of the housing 510 from the open bottom 516 to a top wall 514, the cavity 530 having a substantially cylindrical shape. The top wall 514 further includes an aperture 515 extending a length LA into the housing 510. A stem 528 of an umbrella stopper 518 is at least partially disposed into the aperture 515. The stem 528 may be integrally formed into the aperture 515, while in further embodiments the stem 528 may be non-removably or removably assembled with a threaded connection, press-fit connection, adhesive connection or a combination thereof.

The umbrella stopper 518 further includes a fanned barrier 527, the umbrella stopper 518 and more specifically the fanned barrier 527 being configured as a blockage feature for a lumen 572 extending through the hub 574 of the luer connector 570 of the medical device. In an initial position as shown in FIG. 8A, the fanned barrier 527 of the umbrella stopper 518 creates a liquid tight seal with the inner surface 526 of the cavity 530. The fanned barrier 527 barrier has a substantially conical shape, the edges of the fanned barrier 527 being configured to envelop a portion of the hub 574. The fanned barrier 527 includes a plurality of spines 529 disposed radially from the stem 528, the spines 529 aiding in retaining the conical structure of the fanned barrier 527.

A fluid is disposed within a chamber defined by the fanned barrier 527 and an upper portion of the cavity 530. As shown in FIG. 8B, as the disinfection cap 500 is threaded or pushed against the luer connector to a final position, the fanned barrier 527 elastically deforms into the lumen 572, creating a liquid tight seal while the elastic deformation of the fanned barrier 527 interrupts the liquid tight seal of the fanned barrier 527 and the cavity 530, releasing the fluid which disinfects the hub and the periphery of the luer connector. In the preferred embodiment, the fanned barrier 527 can be made of a deformable elastomeric material such as rubber or TPE.

Figure 9:
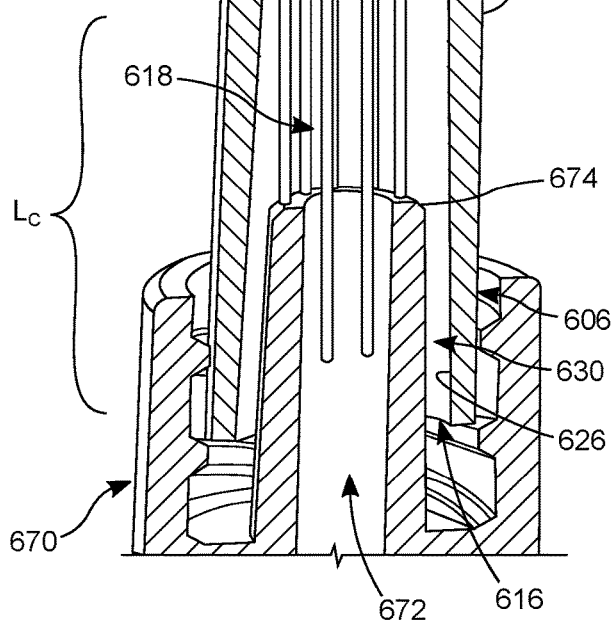
FIG. 9 illustrates a cross-sectional view of a disinfection cap in accordance with a sixth embodiment of the present disclosure.

FIG. 9 depicts an exemplary disinfection cap 600 in accordance with a sixth embodiment of the present disclosure. The disinfection cap 600 includes a housing 610 having an upper portion, a lower portion and an inner surface 626 of the lower portion of the housing 610 defining a cavity 630 having open bottom 616 for receiving a hub of a luer connector. The upper portion of the disinfection cap 600 has a larger diameter than the lower portion, the upper portion serving as a gripping surface for a practitioner to manipulate the disinfection cap 600. In one embodiment, the upper portion is integrally formed with the lower portion while further embodiments are non-removably or removably assembled with a threaded connection, press-fit connection, adhesive connection or a combination thereof.

The cavity 630 of the housing 610 extends a length $L_C$ of the total length of the housing 610 from the open bottom 616 to a top wall 614, the cavity 630 having a substantially cylindrical shape. From the top wall 614 extend a plurality of hydrophilic bristles 618, the hydrophilic bristles 618 extending a distance less than the total length of the cavity 630. The hydrophilic bristles 618 retain a fluid. The hydrophilic bristles act as a blockage feature by preventing the fluid from flowing into a lumen 672 extending through the hub 674 of the luer connector 670 of the medical device. As the disinfection cap 600 is threaded or pushed against the luer connector, the hydrophilic bristles 618 elastically deform, blocking the lumen 672. The hydrophilic bristles 618 are initially bundled upon initial engagement and upon advancement of the hub 674 are compressed into the lumen 672 opening to prevent additional disinfectant inflow. The disinfectant adsorbed to that portion of the bristles is squeezed to the surrounding bristle space to be dispensed to the external lumen surface.

Figure 10A:
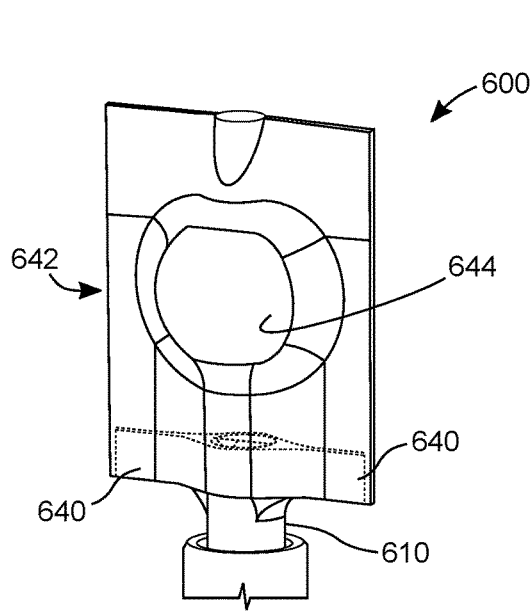
FIG. 10A illustrates a cross-sectional view of a disinfection cap in accordance with a sixth embodiment of the present disclosure.
Figure 10B:
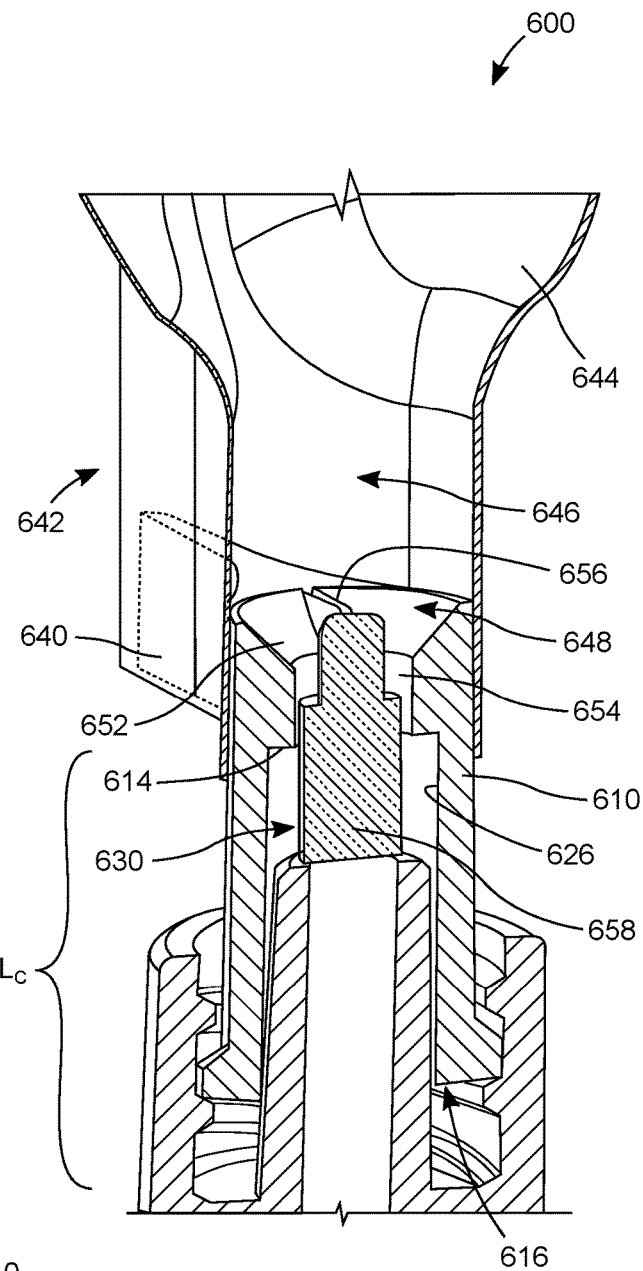
FIG. 10B illustrates a cross-sectional view of a disinfection cap in accordance with the sixth embodiment of the present disclosure; and, FIG. 11 illustrates a cross-sectional view of a disinfection cap in accordance with a seventh embodiment of the present disclosure.

FIGS. 10A and 10B depict an exemplary disinfection cap 600 in accordance with a sixth embodiment of the present disclosure. The disinfection cap 600 includes a housing 610 having an upper portion, a lower portion and an inner surface 626 of the lower portion of the housing 610 defining a cavity 630 having open bottom 616 for receiving a hub of a luer connector. The upper portion of the disinfection cap 600 includes a set of winged protrusions 640 configured to receive a membrane or pouch 642. The membrane or pouch 642 is secured to the winged protrusions 640 with medical grade adhesive. The set of winged protrusions 640 may serve as a gripping feature, aiding a practitioner in twisting or inserting the disinfection cap 600 onto the luer connector. The membrane or pouch 642 includes a bulbous cavity 644 for retaining fluid 602. The bulbous cavity 644 may be depressed or collapsed onto itself by a practitioner, thereby releasing the fluid 602 through a fluid path 646 into a drain 648 of the disinfection cap 600. The drain 648 is disposed on a top surface 650 of the top portion of the disinfection cap 600. A cavity 630 of the housing 610 extends a length $L_C$ of the total length of the housing 610 from the open bottom 616 to a top wall 614, the cavity 630 having a substantially cylindrical shape.

As shown in FIG. 10B, the drain 648 includes a conical cavity 652 in fluid communication with a lumen 654 disposed on a bottom of the conical cavity 652, the lumen 654 being in fluid communication with the cavity 630 of the housing 610. From the top surface 650 extend at least two spines 656, the at least two spines 656 extending into the center of the conical cavity 652. The at least two spines 656 are configured to structurally secure a protrusion 658, the protrusion 658 extending into the conical cavity 652 and lumen 654. The protrusion 658 includes a top portion and a lower portion, the top portion having a smaller diameter than the lower portion. The diameter of the top portion being less than a diameter of the lumen 654 of the drain 648. The lower portion of the protrusion 658 being configured as a blockage feature by which the lower portion has a diameter equal to or greater than the diameter of a hub of the luer connector of the medical device. The lower portion of the protrusion 658 fluidly seals a lumen of the hub of the luer connector when the disinfection cap 600 is threaded or pushed against the luer connector, allowing for the bulbous cavity 644 to be depressed or collapsed, thereby releasing fluid 602. The fluid 602 disinfects the hub and a periphery of the luer connector.

Figure 11:
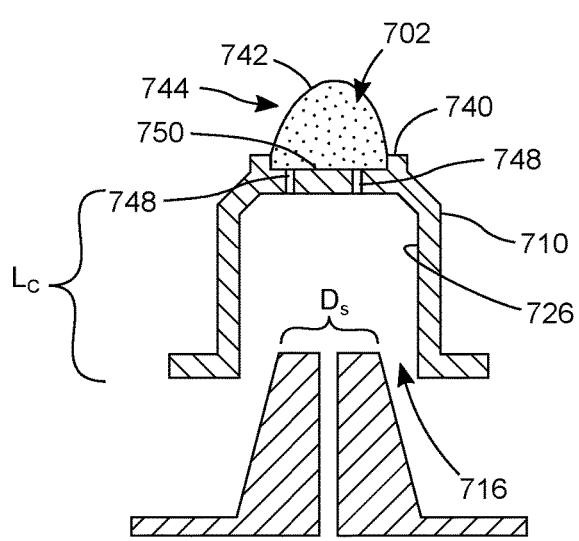

FIG. 11 depicts an exemplary disinfection cap 700 in accordance with a seventh embodiment of the present disclosure. The disinfection cap 700 includes a substantially cylindrical housing 710 having an upper portion, a lower portion and an inner surface 726 of the lower portion of the housing 710 defining a cavity 730 having open bottom 716 for receiving a hub of a luer connector. The upper portion of the disinfection cap 700 includes an engagement surface 740 disposed around a circumference of a top surface 750 of the upper portion of the cylindrical housing 710. The engagement surface 740 is configured to receive a membrane or pouch 742, the membrane or pouch 742 having a dome shape defining a bulbous cavity 744 for retaining fluid 702. The membrane or pouch 742 is secured onto the engagement surface 740 with medical grade adhesive. The bulbous cavity 744 may be depressed or collapsed onto the top surface 850 of the upper portion of the cylindrical housing 710 by a practitioner, thereby releasing the fluid 702 through a fluid path into the cavity 730 of the lower portion of the housing 710. The fluid path is defined by at least two vents or slits 748 disposed through the top surface 750 of the upper portion of the cylindrical housing 710. The slits facilitating fluid communication between the bulbous cavity 744 and the cavity 730 of the lower portion of the housing 710.

The cavity 730 of the housing 710 extends a length $L_C$ of the total length of the housing 710 from the open bottom 716 to a top wall 714, the cavity 730 having a substantially cylindrical shape. The length $L_C$ of the total length of the housing 710 is substantially equal to the length of a hub 774 of a luer connector 770, wherein the top wall 714 is configured to act as a blockage feature for a lumen 772 of the luer connector 770. Abutting the hub 774, the top wall 714 fluidly seals the lumen 772 of the luer connector 770, preventing ingress of fluid 702 from entering the lumen 772 as the fluid 702 is ejected from the at least two slits 748. Likewise, the at least two slits 748 are positioned a distance Ds from one another whereby the at least two slits 748 eject fluid 702, disinfecting the hub and a periphery of the luer connector.

The disinfection cap (100, 200, 300, 400, 500, 600, 700) can achieve disinfection when used on luer connectors by integrating fluid (102, 202, 302, 402, 502, 602, 702) in the cavity (130, 230, 330, 430, 530, 630, 730) of the disinfection cap (100, 200, 300, 400, 500, 600, 700). The fluid (102, 202, 302, 402, 502, 602, 702) can be directly included in the cavity (130, 230, 330, 430, 530, 630, 730). Disinfection cap (100, 200, 300, 400, 500, 600, 700) is designed to be compatible in interacting with various disinfectant or antimicrobial agents or fluid (102, 202, 302, 402, 502, 602, 702). In one or more embodiments, the disinfectant or antimicrobial agent or fluid (102, 202, 302, 402, 502, 602, 702) may include variations of alcohol or chlorhexidine. In one or more embodiments, the disinfectant or antimicrobial agent or fluid (102, 202, 302) may include variations of alcohol or chlorhexidine.

In one or more embodiments, the fluid (102, 202, 302, 402, 502, 602, 702) is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent (102, 202, 302, 402, 502, 602, 702) is a fluid or a gel.

In one or more embodiments, the disinfection cap (100, 200, 300, 400, 500, 600, 700) can include a removable peel seal covering the opening to the cavity (130, 230, 330, 430, 530, 630, 730). In one or more embodiments, the peelable seal comprises an aluminum or multi-layer polymer film peel back top. In a specific embodiment, the peelable is heat-sealed or induction sealed to the open end of the disinfection cap (100, 200, 300, 400, 500, 600, 700). In one or more embodiments, the peelable seal comprises a moisture barrier.

The disinfection cap (100, 200, 300, 400, 500, 600, 700) is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the disinfection cap (100, 200, 300, 400, 500, 600, 700) comprises a polypropylene or polyethylene material.

In one or more embodiments, the connector of the medical device may be selected from the group consisting essentially of needle-free connectors, catheter luer connectors, stopcocks, and hemodialysis connectors on primary IV gravity sets, secondary IV gravity sets, extension sets, and infusion or syringe pump sets. In some embodiments, the disinfection cap can be connected with any of a variety of different needleless injection sites. In one or more embodiments, after the disinfection cap has been coupled with connector, it is unnecessary to disinfect (e.g., treat with an alcohol swab) the connector prior to each reconnection of the connector with another connector, as the connector will be kept in an uncontaminated state while coupled with the disinfection cap. Use of the disinfection cap (100, 200, 300, 400, 500, 600, 700) replaces the standard swabbing protocol for cleaning connectors.

Yet another aspect of the present disclosure pertains to a method of disinfecting a medical connector. The method comprises connecting the disinfection cap (100, 200, 300, 400, 500, 600, 700) of one or more embodiments to a medical connector, wherein connecting includes engaging the threads of the medical connector onto the threads on the outer surface of the sidewall of the housing (110, 210, 310, 410, 510, 610, 710) of the disinfection cap upon insertion of the medical connector into the disinfection cap (100, 200, 300, 400, 500, 600, 700) such that the medical connector contacts the blockage feature.

A further aspect of the present disclosure pertains to an assembly. The assembly comprises the disinfection cap (100, 200, 300, 400, 500, 600, 700) of one or more embodiments connected to a medical connector. In one or more embodiments, the medical connector is selected from a luer connector, or other needleless connector having a fitting. In one or more embodiments, the luer connector may be selected from the group consisting essentially of needle-free connectors, catheter luer connectors, stopcocks, and hemodialysis connectors.

A further aspect of the present disclosure pertains to packaging. In one or more embodiments, disinfection cap (100, 200, 300, 400, 500, 600, 700) can be packaged into a strip configuration. The strip configuration may comprise a single-piece top web on which multiple caps (100, 200, 300, 400, 500, 600, 700) are attached through a sealing layer. The strip configuration may also comprise individually sealed caps with individual top web foil, and then a series of individually sealed caps are attached to a piece of strip composed of materials such as plastic in an arrayed fashion. The individual top web foil can have a tab that is attached to the strip material through adhesive or through sealant.

It is contemplated that the disinfection cap (100, 200, 300, 400, 500, 600, 700) disclosed herein and shown in the Figures may also be utilized with female luer connectors, including female luer connectors, wherein the blockage feature can be used to block the lumen of open luers to facilitate the mitigation of such disinfectant ingress into connectors, thereby reducing risk of the disinfectant entering the blood stream. It is therefore contemplated that the disinfection cap (100, 200, 300, 400, 500, 600, 700) disclosed herein and shown in the Figures may be utilized with both and female luer connectors.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the claims.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection cap comprising:
a housing;
a top wall;
a cylindrical sidewall having an inner surface defining a cavity;
an open bottom formed by the cylindrical sidewall with an opening to the cavity within said housing for receiving a hub of a luer connector;
a first depressible open cell foam structure disposed within the cavity;
a blockage feature disposed on the first depressible open cell foam structure, the blockage feature configured as a protrusion, wherein the protrusion further includes an upper portion and a lower portion, the lower portion configured to fluidly block the hub of the luer connector, and a second depressible open cell foam structure abutting and disposed on top of the first open cell foam structure and configured to fit around the lower portion of the protrusion;
a first fluid releasably retained within the first depressible open cell foam structure disposed within the cavity, a second fluid releasably retained within the second depressible open cell foam structure, the first open cell foam structure and the second open cell foam structure have the same outer diameters; and
at least one thread on an outer surface of the housing.

2. The disinfection cap of claim 1, wherein said cavity extends from an inner surface of said top wall toward said open bottom of said housing.

3. The disinfection cap of claim 1, wherein the protrusion is disposed on the bottom surface of the first open cell foam structure.

4. The disinfection cap of claim 1, wherein the first depressible open cell foam structure is disposed against the top wall, the second depressible open cell foam structure having a hollow cylindrical shape configured to fit around the protrusion.

5. The disinfection cap of claim 1, the upper portion of the protrusion having a diameter equal to the top wall, the lower portion of the protrusion having a diameter smaller than the upper portion.

6. The disinfection cap of claim 5, wherein the second depressible open cell foam structure is disposed against a bottom surface of the upper portion of the protrusion, the second depressible open cell foam structure having a hollow cylindrical shape configured to fit around the lower portion of the protrusion.

7. The disinfection cap of claim 5, wherein the first depressible open cell foam structure is disposed between the upper portion of the protrusion and the top wall of the cavity.

8. The disinfection cap of claim 1, said at least one thread being sufficient to interlock with a mating feature of said luer connector.

9. The disinfection cap of claim 8, wherein said hub is secured within said inner surface of said cavity by interlocking at least a portion of said at least one thread with a mating feature on said hub of said luer connector.

10. The disinfection cap of claim 1, wherein the inner surface of the cavity is secured by an interference fit with the hub of the luer connector.

11. The disinfection cap of claim 1, wherein the first fluid is selected from a group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

12. The disinfection cap of claim 1, wherein the protrusion is cylindrical.

13. The disinfection cap of claim 7, wherein the second fluid is selected from a group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

* * * * *